(12) United States Patent
Sircar et al.

(10) Patent No.: US 6,699,888 B2
(45) Date of Patent: Mar. 2, 2004

(54) INHIBITORS OF $\alpha_L\beta_2$ MEDIATED CELL ADHESION

(75) Inventors: Ila Sircar, San Diego, CA (US); Yun Feng Xie, San Diego, CA (US); Nicholas Smith, San Diego, CA (US); Paul S. Furth, Bonita, CA (US)

(73) Assignee: Tanabe Seiyaku Co., Ltd., Osaka (JP)

( * ) Notice: Subject to any disclaimer, the term of this patent is extended or adjusted under 35 U.S.C. 154(b) by 0 days.

(21) Appl. No.: 10/296,907

(22) PCT Filed: Apr. 17, 2001

(86) PCT No.: PCT/US01/12323

§ 371 (c)(1),
(2), (4) Date: Jan. 27, 2003

(87) PCT Pub. No.: WO01/92253

PCT Pub. Date: Dec. 6, 2001

(65) Prior Publication Data

US 2003/0225138 A1 Dec. 4, 2003

Related U.S. Application Data

(60) Provisional application No. 60/207,968, filed on May 31, 2000.

(51) Int. Cl.[7] ................. A61K 31/4439; C07D 401/04
(52) U.S. Cl. ..................................... 514/341; 546/274.1
(58) Field of Search ..................... 514/341; 546/274.1

(56) References Cited

U.S. PATENT DOCUMENTS 4,944,791 A    7/1990   Schroder et al.

6,350,763 B1 * 2/2002  Kelly et al. ............... 514/341

FOREIGN PATENT DOCUMENTS

EP    0 770 613 A      5/1997
WO    WO 01 07048 A    2/2001

OTHER PUBLICATIONS

Kelly, Terence A. et al., J. Immunol. , vol. 163(10), pp. 5173–5177, 1999.

* cited by examiner

*Primary Examiner*—Charanjit S. Aulakh
(74) *Attorney, Agent, or Firm*—Birch, Stewart, Kolasch & Birch, LLP

(57) ABSTRACT

The present invention relates to small molecules according to formula (I) that are potent inhibitors of $\alpha_L\beta_2$ mediated cell adhesion and which could be useful for the treatment of inflammatory diseases:

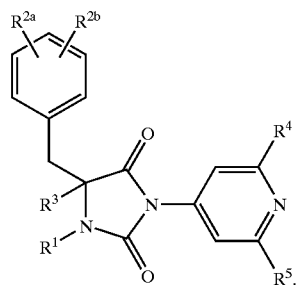

14 Claims, No Drawings

INHIBITORS OF $\alpha_L\beta_2$ MEDIATED CELL ADHESION

This application is the national phase under 35 U.S.C. §371 of PCT International Application No. PCT/US01/12323 now WO 01/92253, which has an International filing date of Apr. 17, 2001, which designated the United States of America. This application claims priority on provisional Application No. 60/207,968 filed on May 31, 2000, the entire contents of which are hereby incorporated by reference.

BACKGROUND OF THE INVENTION

1. Field of the Invention

The present invention relates to small molecules that are potent inhibitors of $\alpha_L\beta_2$ mediated cell adhesion which could be useful for the treatment of inflammatory diseases.

2. Description of Related Art

The integrin family of proteins are heterodimeric receptors which are expressed on all cell types to mediate cell to cell binding and adhesion to extracellular matrix. The $\beta_2$ (CD18) integrin subfamily is comprised of 3 members, $\alpha_L\beta_2$ integrin (LFA-1, CD11a/CD18), $\alpha_M\beta_2$ integrin (Mac-1, CD11b/CD18), and gp 150 $\beta_2$ integrin ($\alpha_X\beta_2$ integrin, CD11c/CD18) that are primarily expressed on leukocytes (Sanchez-Madrid et al., J. Exp. Med., 158, 1785–1803 (1983)). $\alpha_L\beta_2$ integrin is found mostly on T and B lymphocytes, while $\alpha_M\beta_2$ integrin is present on activated neutrophils, NK cells and some myeloid cells. The $\alpha_L\beta_2$ integrin binds to intracellular adhesion molecules ICAM-1, 2 and 3 found on multiple cell types such as vascular endothelial cells, dendritlc cells, epithelial cells, macrophage and T lymphoblasts (Dustin et al., J. Immunology, 137, 245–254 (1986)). Recently there has been evidence presented that $\alpha_L\beta_2$ integrin binds to ICAM-4 and a novel ligand expressed in brain telencephalin. It has been shown that the I domain or the alpha chain is the major recognition site for its ligands.

$\alpha_L\beta_2$ integrin adhesion to ICAM-1 is necessary for immune responsiveness of T-lymphocytes to antigens, lymphocyte homing and circulation, and cell emigration to sites or inflammation (Springer, Ann. Rev. Physiol., 57, 827 (1995)). A dominant role of $\alpha_L\beta_2$ integrin in mediating inflammatory events is shown in several different animal models of inflammatory diseases in which antibodies to $\alpha_L\beta_2$ integrin or ICAM-1 significantly inhibit development of therapeutic end points (Rothlein et al., Kidney International, 41, G17 (1992); Iigo et al., J. Immunology, 147, 4167 (1991); Bennet et al., J. Pharmacol. and Exp. Therapeutics, 280, 988 (1997)).

Also, $\beta_2$ integrin subfamily are thought to play a critical role in several types of inflammatory disease processes by interacting with ICAMs. Support for the importance of $\beta_2$ integrin in mediating inflammatory responses has been demonstrated by the evidence that transendothelial migration in vitro is markedly inhibited by monoclonal antibodies against $\beta_2$ integrin or ICAM-1 (Smith, Can. J. Physiol. Pharmacol., 71, 76 (1993)). Furthermore, blockade of $\alpha_L\beta_2$ integrin has been shown to inhibit neutrophil influx in almost every system, including skin, peritoneum, synovium, lung, kidney, and heart. As one of the primary ligands for the $\beta_2$ integrin, it would also be expected that blockade of ICAM-1 would inhibit the inflammatory response (Albelda et al., The FASEB Journal, 8, 504 (1994)).

Moreover, it has been shown that antibodies against $\alpha_L\beta_2$ integrin suppress rejection after transplantation. WO 94/04188 discloses the use of monoclonal antibodies directed against $\alpha_L\beta_2$ integrin for all transplantations, including graft vs. host or host vs. graft diseases.

SUMMARY OF THE INVENTION

The present invention relates to a compound of the formula (I):

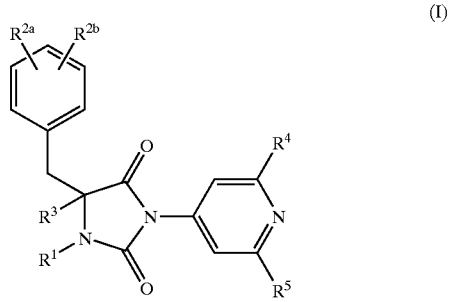

or a pharmaceutically acceptable salt thereof, wherein $R^1$ is selected from 1) hydrogen atom, or
2) a $C_{1-6}$ alkyl group which may be optionally substituted with a carboxyl group or a $C_{1-6}$ alkoxycarbonyl group; $R^{2a}$ and $R^{2b}$ are independently hydrogen atom, a halogen atom, hydroxyl group, cyano group, a $C_{1-6}$ alkyl group which may be optionally substituted with 1 to 3 halogen atoms, a $C_{1-6}$ alkylthio group which may be optionally substituted with 1 to 3 halogen atoms, a $C_{1-6}$ alkylsulfinyl group which may be optionally substituted with 1 to 3 halogen atoms, a $C_{1-6}$ alkylsulfonyl group which may be optionally substituted with 1 to 3 halogen atoms, or a $C_{1-6}$ alkoxy group which may be optionally substituted with 1 to 3 halogen atoms; $R^3$ is a $C_{1-6}$ alkyl group; and $R^4$ and $R^5$ are independently a halogen atom.

The compound of the present invention has potent inhibitory activity against $\alpha_L\beta_2$ mediated cell adhesion, and shows excellent in vivo improvements against the unfavorable conditions caused by $\alpha_L\beta_2$ mediated cell adhesion.

DETAILED DESCRIPTION OF THE INVENTION

The desired compound of the present invention may exist in he form of optical isomers based on asymmetric atoms thereof, and the present invention also includes these optical isomers and mixtures thereof.

In an embodiment of the present invention, the steric configuration of a bond need not be fixed. The compound of the present invention may be a compound with a sole configuration or a mixture with several different configurations.

In a preferred embodiment of the compound (I), $R^1$ is hydrogen atom or a $C_{1-6}$ alkyl group which may be optionally substituted with carboxyl group or a $C_{1-6}$ alkoxycarbonyl group, $R^{2a}$ and $R^{2b}$ are independently hydrogen atom, a halogen atom, hydroxyl group, cyano group or a $C_{1-6}$ alkoxy group which may be optionally substituted with 1–3 halogen atoms, $R^3$ is a $C_{1-6}$ alkyl group, and $R^4$ and $R^5$ are independently a halogen atom.

In a more preferred embodiment of the compound (I), $R^1$ is hydrogen atom or a $C_{1-6}$ alkyl group, one of $R^{2a}$ and $R^{2b}$ is hydrogen atom, and the other is a halogen atom, cyano group, or a $C_{1-6}$ alkoxy group which may be optionally substituted with 1–3 halogen atoms, $R^3$ is a $C_{1-6}$ alkyl group, and $R^4$ and $R^5$ are independently a halogen atom.

In a further preferred embodiment of the compound (I), $R^1$ is hydrogen atom or methyl group, one of $R^{2a}$ and $R^{2b}$ is hydrogen atom and the other is bromine atom, cyano group, a $C_{1-6}$ alkoxy group or trifluoromethoxy group, $R^3$ is methyl group, $R^4$ and $R^5$ are chlorine atom.

In another more preferred embodiment of the compound (I), $R^1$ is hydrogen atom or $C_{1-6}$ alkyl group which may be substituted with carboxyl or $C_{1-6}$ alkoxycarbonyl, one of $R^{2a}$ and $R^{2b}$ is hydrogen atom, and the other is cyano group or $C_{1-6}$ alkoxy group which may be substituted with 1–3 halogen atoms.

In another further preferred embodiment of the compound (I), $R^1$ is hydrogen atom or methyl group, one of $R^{2a}$ and $R^{2b}$ is hydrogen atom and the other is $C_{1-6}$ alkoxy group or trifluoromethoxy group, $R^3$ is methyl group, $R^4$ and $R^5$ are chlorine atom.

In another preferred embodiment of the compound (I), $R^1$ is a $C_{1-6}$ alkyl group which is substituted with a $C_{1-6}$ alkoxycarbonyl group or carboxyl group, one of $R^{2a}$ and $R^{2b}$ is hydrogen atom, and the other is a halogen atom, cyano group, or $C_{1-6}$ alkoxy group which may be optionally substituted with 1–3 halogen atoms, $R^3$ is a $C_{1-6}$ alkyl group, and $R^4$ and $R^5$ are independently a halogen atom.

In a more preferred embodiment of the compound (I), $R^3$ is methyl group, and $R^4$ and $R^5$ are chlorine atom.

Most preferred compound of the present invention is selected from:

3-(2,6-Dichloro-4-pyrydyl)-5-(4-bromobenzyl)-1,5-dimethyl-2,4-imidazolidinedione, 3-(2,6-Dichloro-4-pyrydyl)-5-(4-propoxybenzyl)-1,5-dimethyl-2,4-imidazolidinedione, 3-(2,6-Dichloro-4-pyrydyl)-5-(4-ethoxybenzyl)-1,5-dimethyl-2,4-imidazolidinedione, 3-(2,6-Dichloro-4-pyrydyl)-5-(4-(1,1,1trifluoromethoxybenzyl)]-5-methyl-2,4-imidazolidinedione, 3-(2,6-dichloro-4-pyrydyl)-5-[4-(1,1,1trifluoromethoxybenzyl)]-1,5-Dimethyl-2,4-imidazolidinedione, 3-(2,6-Dichloro-4-pyrydyl)-5-(4-Cyanobenzyl)-5-methyl-2,4-imidazolidinedione, 3-(2,6-Dichloro-4-pyrydyl)-5-(4-Cyanobenzyl)-1,5-dimethyl-2,4-imidazolidinedione; and a pharmaceutically acceptable salt of these compounds.

The compound of the present invention has potent inhibitory activity against $\alpha_L\beta_2$ mediated cell adhesion, and also shows excellent bioavailability after oral administration which reflects the overall improvement in plasma protein binding and solubility. The compound of the present invention therefore shows excellent in viva improvements against the unfavorable conditions caused by $\alpha_L\beta_2$ mediated cell adhesion.

The compound of the present invention may be clinically used either in a free form or in the form of pharmaceutically acceptable salts thereof. Pharmaceutically acceptable salts include an acid-addition salt with an inorganic acid or an organic acid (e.g., hydrochloride, sulfate, nitrate, hydrobromide, methanesulfonate, p-toluenesulfonate, acetate), and a salt with an inorganic base, an organic base or an amino acid (e.g., triethylamine salt, a salt with lysine, an alkali metal salt, an alkali earth metal salt and the like).

Pharmaceutically acceptable salts also include an intramolecular salt thereof, or a solvate or hydrate thereof.

The compound of the present invention may be formulated into a pharmaceutical composition comprising a therapeutically effective amount of the compound as defined above and a pharmaceutically acceptable carrier or diluent. The pharmaceutically acceptable carrier or diluent may be, for example, binders (e.g., syrup, gum arabic, gelatin, sorbitol, tragacanth, polyvinylpyrrolidone), excipients (e.g., lactose, sucrose, corn starch, potassium phosphate, sorbitol, glycine), lubricants (e.g., magnesium stearate, talc, polyethylene glycol, silica) disintegrators (e.g., potato starch), wetting agents (e.g., sodium laurylsulfate), and the like.

The desired compound of the present invention or pharmaceutically acceptable salts thereof may be administered either orally or parenterally, and it may be used as a suitable pharmaceutical preparation. These pharmaceutical preparations may be in the form of a solid preparation such as a tablet, a granule, a capsule, and a powder, or in the form so a liquid preparation such as solution, suspension, and emulsion, when administered orally. When administered parenterally, the pharmaceutical preparation may be in the form of suppository, an injection preparation or an intravenous drip preparation using distilled water for injection, a physiological salt solution, an aqueous glucose solution, and so on, and an inhalation by a conventional process.

The dose of the desired compound of the present invention or a pharmaceutically acceptable salt thereof varies depending on an administration method, age, sex, body weight, and condition of a patient, but, in general, the daily dose is preferably about 0.1 to 100 mg/kg/day, particularly preferably 1 to 100 mg/kg/day.

The compound of the present invention can be used for treating or preventing $\alpha_L\beta_2$ adhesion mediated conditions in a mammal such as a human.

The compound of the present invention may be used for treatment or prevention of numerous inflammatory diseases such as rheumatoid arthritis, asthma, allergy conditions, adult respiratory distress syndrome, AIDS, cardiovascular diseases, thrombosis, harmful platelet aggregation, reocclusion following thrombolysis, reperfusion injury, skin inflammatory diseases (e.g., psoriasis, eczema, contact dermatitis, atopic dermatitis), osteoporosis, osteoarthritis, arteriosclerosis (including atherosclerosis), neoplastic diseases including metastasis of neoplastic or cancerous growth, wound, detaching retina, Type I diabetes, multiple sclerosis, systemic lupus erythematosus (SLE), ophthalmic inflammatory conditions, inflammatory bowel diseases (Crohn's disease and ulcerative colitis), regional enteritis, Sjogren's Syndrome, and other autoimmune diseases.

The compound of the present invention may also be used for the rejection (i.e., chronic rejection and acute rejection) after transplantation, including allograft rejection (host vs. graft disease) and graft vs. host disease.

The compound of the present invention may be preferably used for treatment or prevention of psoriasis, rheumatoid arthritis, inflammatory bowel diseases (Crohn's disease, ulcerative colitis), systemic lupus erythematosus, atopic dermatitis, Sjogren's syndrome, and rejection after transplantation (allograft rejection and graft vs. host disease).

According to the present invention, the desired compound (I) can be prepared by the following methods:

Method A:

Among the desired compound (I), a compound of the formula (I-a):

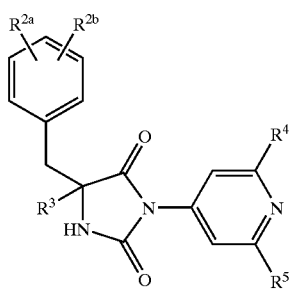

(I-a)

wherein the symbols are the same as defined above, or a pharmaceutically acceptable salt thereof, can be prepared by (1) cyclizing the compound of the formula (II):

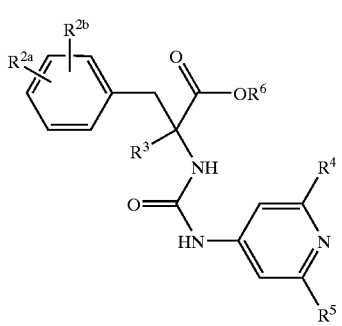

(II)

wherein $OR^6$ is a hydroxyl group or a protected hydroxyl group, and the other symbols are the same as defined above, and (2) converting the resulting cyclized compound into a pharmaceutically acceptable salt thereof by a conventional method, if desired.

When $OR^6$ is a protected hydroxyl group, the protecting group can be selected from the conventional protecting groups for a carboxyl group (i.e., a $C_{1-6}$ alkyl group, benzyl group).

The cyclization can be carried out by a conventional condensation method. For example, the cyclization of the compound (II) can be carried out in the presence of an acid or a base in a suitable solvent.

The acid can be selected from organic acids (i.e., p-toluenesulfonic acid, and trifluoroacetic acid) and inorganic acids (i.e., hydrochloric acid, sulfuric acid, and nitric acid).

The base can be selected from conventional bases such as alkali metal alkoxide (e.g., NaOEt, NaOMe).

The solvent can be selected from any one which does not disturb the cyclization reaction, for example, $CH_2Cl_2$, THF, DMF, alcohols (methanol, ethanol, etc.) or a mixture thereof. The reaction is carried out at a temperature of 0° C. to boiling point of the solvent, preferably at 50° C. to 100° C.

The cyclization of the compound (II) is also carried out in the presence of a condensing reagent with or without a base in a suitable solvent or without a solvent. The condensing reagent can be selected from $SOCl_2$ and conventional condensing reagents which can be used for a peptide synthesis, for example, BOP-Cl, BOP reagent, DCC, EDC or CDI.

The base can be selected from an organic base (e.g., DIEA, DMAP, DBU, $Et_3N$), an alkali metal hydride (e.g., NaH, LiH), an alkali metal carbonate (e.g., $Na_2CO_3$, $K_2CO_3$), an alkali metal hydrogen carbonate (e.g., $NaHCO_3$, $KHCO_3$), an alkali metal amide (e.g., $NaNH_2$), an alkali metal alkoxide (e.g., NaOMe, KOMe), a $C_{1-6}$ alkyl alkali metal salt(e.g., n-BuLi, t-BuLi), an alkali metal hydroxide (e.g., NaOH, KOH), an alkaline earth metal hydroxide (e.g., $Ba(OH)_2$), and the like.

The solvent can be selected from any one which does not disturb the cyclization reaction, for example, $CH_2Cl_2$, THF, DMF or a mixture thereof. The reaction is carried out at a temperature of 0° C. to room temperature, preferably at room temperature.

Method B

Among the desired compound (I), a compound of the formula (I-b):

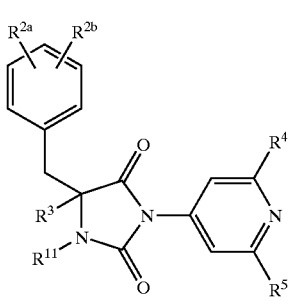

(I-b)

wherein $R^{11}$ is a $C_{1-6}$ alkyl group which may be optionally substituted with carboxyl group or a $C_{1-6}$ alkoycarbonyl group and the other symbols are the same as defined above, or a pharmaceutically acceptable salt thereof, may be prepared by:

(1) alkylating the compound (I-a), (2) hydrolyzing the resulting compound, if necessary, and (3) converting the resulting compound into a pharmaceutically acceptable salt thereof by a conventional method, if further desired.

(1) Alkylation Reaction

The alkylation reaction can be carried out by reacting the compound (I-a) with the compound of the formula (III):

$$R^{11}-X \qquad (III)$$

wherein X is a leaving group and $R^{11}$ is the same as defined above.

The leaving group X can be selected from conventional leaving groups, such as a halogen atom (e.g., chlorine, bromine, iodine) and an alkylsulfonyloxy group or an arylsulfonyloxy group (e.g., methylsulfonyloxy group, p-tolylsulfonyloxy group).

The alkylation reaction can be carried out in the presence of a base in a suitable solvent.

The base can be selected from conventional bases such as alkali metal hydride (i.e., NaH, KH), alkali metal alkoxide (i.e., NaOMe, NaOEt) and alkali metal amide (i.e., $NaNH_2$, LDA, KHMDS).

The solvent can be selected from any one which does not disturb the condensation reaction, for example, DME, THF, DMF, HMPA or a mixture thereof. The reaction is carried out at a temperature of -78° C. to room temperature.

(2) Hydrolysis Reaction

The compound (I-b) wherein $R^{11}$ is a $C_{1-6}$ alkyl group substituted with carboxyl group can be prepared by hydrolyzing the compound (I-b) wherein $R^{11}$ is a $C_{1-6}$ alkyl group substituted with a $C_{1-6}$ alkoxycarbonyl group. The hydrolysis can be carried out by a usual procedure, for example, by treating the compound with a base in a suitable solvent. The base can be selected from conventional inorganic bases such as LiOH, NaOH and KOH. The solvent can be selected from any one which does not disturb the hydrolyzing reaction, for example, THF, MeOH, EtOH, H$_2$O or a mixture thereof. The reaction can be carried out at a temperature of −78° C. to 50° C., preferably at a temperature of 0° C. to room temperature.

Method C

Among the desired compound (I), the compound of the formula (I-c):

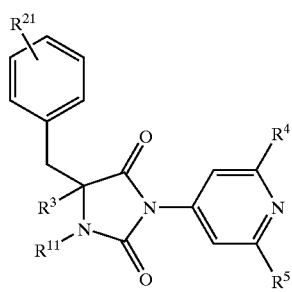

(I-c)

or a pharmaceutically acceptable salt thereof, wherein $R^{21}$ is a $C_{1-6}$ alkoxy group and the other symbols are the same as defined above, can be prepared by alkylating a compound of the formula (I-d):

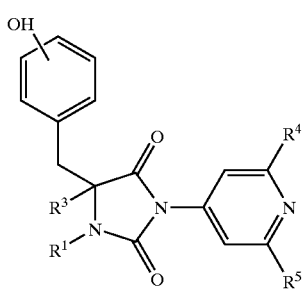

(I-d)

wherein the symbols are the same as defined above, and converting into the pharmaceutically acceptable salt, if desired.

The alkylation reaction can be carried out in a similar manner as described in Method B (1) using a suitable halogenated $C_{1-6}$ alkane (e.g., methyl iodide, benzyl bromide) in the presence of a base (e.g., Et$_3$N, DIEA, NaHCO$_3$, KHCO$_3$, Na$_2$CO$_3$, K$_2$CO$_3$, KHCO$_3$, CsCO$_3$) at a temperature of 0° C. to 50° C. in an organic solvent (e.g., CH$_2$Cl$_2$, THF, DMF, CH$_3$CN, toluene).

The compound (I) wherein $R^{2a}$ and/or $R^{2b}$ are hydroxyl groups can be prepared by the demethylation of the compound (I) wherein $R^{2a}$ and/or $R^{2b}$ methoxy group. The demethylation reaction can be carried out by a conventional method, for example, a treatment with BBr$_3$ or HBr at a temperature of −78° C. to 50° C. in a suitable solvent (e.g., AcOH, water).

The starting compound of the formula (II) can be prepared by the following scheme: Scheme 1.

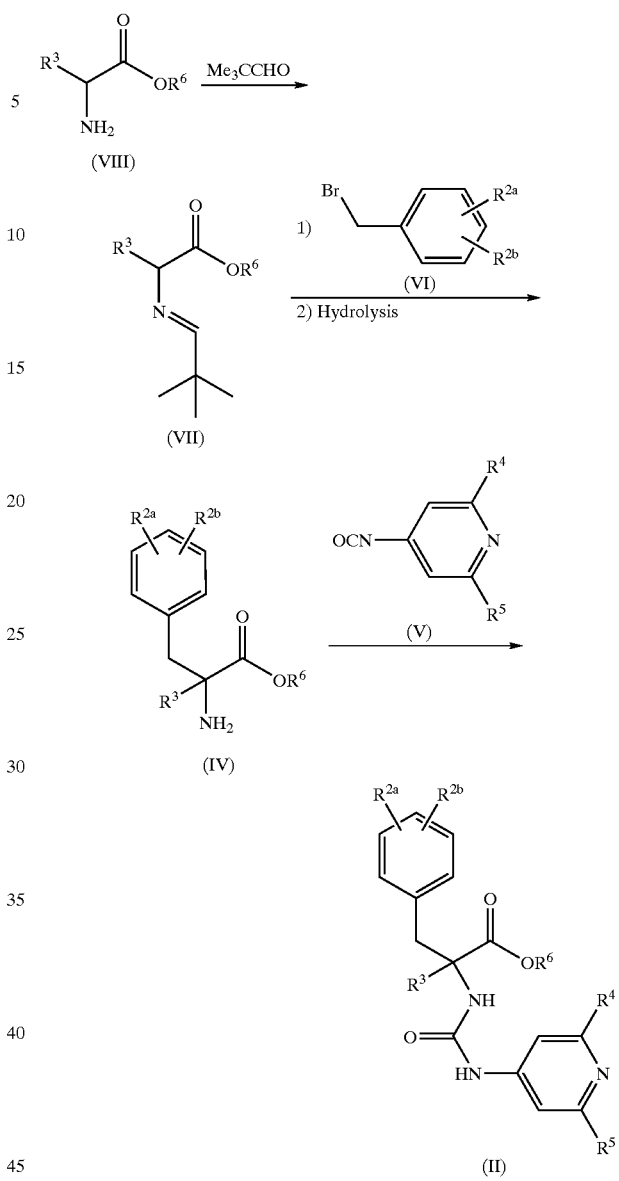

(In the Scheme 1, the symbols are the same as defined above.)

Step 1: The compound (VII) can be prepared by reacting the compound (VIII) with pivalaldehyde. The reaction can be carried out in the presence or absence of an acid or an acidic salt in a suitable solvent or without a solvent. The acid can be selected from conventional inorganic acid such as HCl, H$_2$SO$_4$. The acidic salt can be selected from a salt of a strong inorganic acid and a weak inorganic base such as MgSO$_4$. The solvent can be selected from any one which does not disturb the reaction, for example, toluene, DME, DMF, THF, CH$_2$Cl$_2$ or a mixture thereof. The reaction can be carried out, for example, at a temperature of 0° C. to room temperature.

Step 2: The compound (IV) can be prepared by 1) reacting the compound (VII) with the compound (VI), and 2) hydrolyzing the resulting compound.

The reaction of the compound (VII) and the compound (VI) can be carried out in the presence of a base in a suitable solvent or without a solvent. The base can be selected from conventional bases such as alkali metal alkoxides (e.g., t-BuOK, MeONa, EtONa) and alkali metal amides (e.g., LDA, NaNH$_2$). The solvent can be selected from any one which does not disturb the coupling reaction, for example, toluene, DME, DMF, THF, CH$_2$Cl$_2$ or a mixture thereof. The reaction can be carried out, for example, at a temperature of −78° C. to 50° C., preferably at a temperature of −10° C. to 0° C.

Hydrolysis can be carried out in the presence of an acid in a suitable solvent or without a solvent. The acid can be selected from conventional inorganic acid such as HNO$_3$, HCl, and H$_2$SO$_4$. The solvent can be selected from any one which does not disturb the reaction, for example, toluene, DME, DMF, THF, CH$_2$Cl$_2$ or a mixture thereof. The reaction can be carried out, for example, at a temperature of 0° C. to room temperature.

Step 3: The compound (II) can be prepared by reacting the compound (IV) with the compound (V).

The reaction can be carried out in the presence or absence of a base in a suitable solvent or without a solvent. The base can be selected from conventional inorganic bases such as K$_2$CO$_3$, Na$_2$CO$_3$ and NaHCO$_3$, and conventional organic bases such as pyridine, Et$_3$N, iPr$_2$EtN, aniline, and N,N-dimethylaniline. The solvent can be selected from any one which does not disturb the coupling reaction, for example, toluene, DME, DMF, THF, CH$_2$Cl$_2$ or a mixture thereof. The coupling reaction can be carried out, for example, at a temperature of −78° C. to 50° C., preferably at a temperature of 0° C. to room temperature.

In the present description and the claims, the C$_{1-6}$ alkyl group means a straight chain or branched chain alkyl group having 1 to 6 carbon atoms, for example, methyl group, ethyl group, propyl group, isopropyl group, butyl group, isobutyl group, etc., preferably one having 1 to 4 carbon atoms. The C$_{1-6}$ alkoxy means a straight chain or branched chain alkoxy group having 1 to 6 carbon atoms, for example, methoxy group, ethoxy group, propoxy group, isopropoxy group, butoxy group, isobutyloxy, etc., preferably one having 1 to 4 carbon atoms.

Abbreviations

AcOEt: Ethyl acetate (=EtOAc)
BSA: Bovine serum albumin
DMF: Dimethyl formamide
DCM: Dichloromethane
DIEA: Diisopropylethylamine
DMSO: Dimethyl sulfoxide
Et: Ethyl
EtOH: Ethanol
HBSS: Hank's balanced salt solution
HMPA: Hexamethylphosphoramide
HSA: Human serum albumin
KHDS: Potassium hexamethyldisilazide (=Potassium bis(trimethylsilyl)amide)
LDA: Lithium diisopropylamide
Me: Methyl
MeOH: Methanol
n-Bu: n-Butyl
Ph: Phenyl
t-Bu: tert-butyl
THF: Tetrahydrofuran
Tf: Trifluoromethanesulfonyl
TFA: Trifluoroacetic acid The compound of the present invention is exemplified by the following examples but not limited thereby.

EXAMPLES

Example 1

3-(2,6-Dichloro-4-pyridyl)-5-(4-cyanobenzyl)-5-methyl-2,4-imidazolidinedione

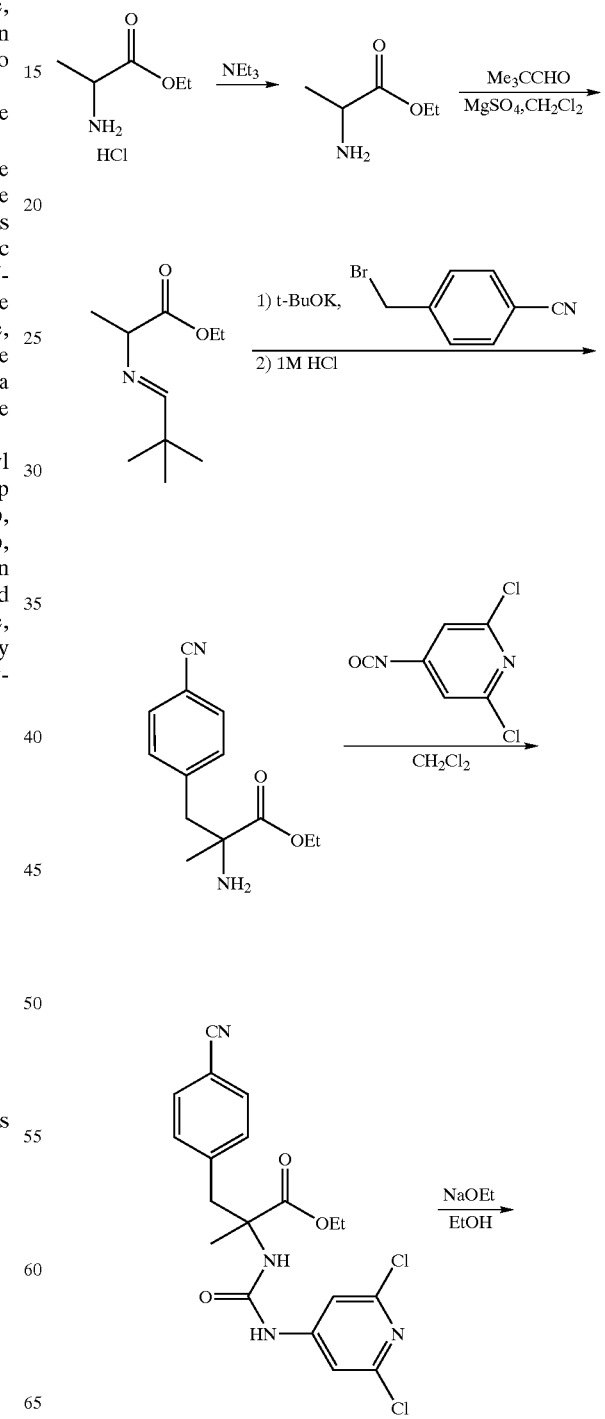

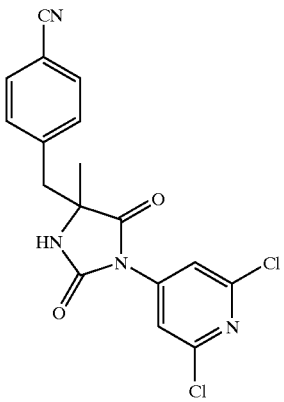

Step-1. L-Alanine ethyl ester hydrogen chloride salt (15 g) was dissolved in H₂O (60 ml). NEt₃(10.9 g) was added to the stirring solution. The solution was allowed to stir for 30 minutes at room temperature and extracted with EtOAc. The combined organic layers were dried over Na₂SO₄, filtered and evaporated to give 9.5 g of L-Alanine ethyl ester. The product was used directly for next step. MS: 118 (MH⁺).

Step-2. L-Alanine ethyl ester from step-1 (9 g) was dissolved in 150 ml anhydrous CH₂Cl₂. The solution was cooled to 0° C. MgSO₄ (10.17 g) was added to the solution followed by addition of pivalaldehyde (6.95 g). The reaction mixture was allowed to warm to room temperature and stirred overnight. The reaction mixture was filtered and the filtrate was evaporated to give 11.2 g of N-neopentylidene-L-alanine ethyl ester. The product was used for next step without further purification. MS: 186 (MH⁺).

Step-3. 4-Cyanobenzyl bromide (4.6 g) was added to a solution of the compound obtained from step 3 (4 g) in anhydrous toluene (40 mL). The resulting mixture was cooled to −10° C. t-BuOK (2.9 g) was added portionwise maintaining the temperature at 0° C. The reaction mixture was stirred at that temperature for 4 hours. The mixture was partitioned between EtOAc/H₂O. The combined organic layers were dried over Na₂SO₄, filtered and concentrated. 1 M HCl was added (40 mL) to the residue and the resulting mixture was allowed to stir overnight. EtOAc was added and the reaction mixture was allowed to stir for 30 minutes. The organic phase was separated and the aqueous layer was extracted with additional EtOAc. The combined organic layers were washed with H₂O. The pH of the combined aqueous solution was adjusted to approximately 8 with solid NaHCO₃, and the mixture was extracted with EtOAc. The combined organic layers were dried over Na₂SO₄, filtered and concentrated to yield ethyl 2-amino-2-(4-cyanobenzyl) propanoate that was used directly for the next step. MS: 233 (MH⁺).

Step-4. 2,6-Dichloro-4-pyridyl isocyanate (1 g) was added to a solution of the compound obtained from step-3 (1.35 g) in anhydrous CH₂Cl₂ (10 mL) maintained at 0° C. The reaction mixture was allowed to warm to room temperature and stirred overnight. The mixture was partitioned between EtOAc/H₂O. The combined organic layers were dried over Na₂SO₄, filtered and concentrated to give 2-(4-cyanobenzyl)-5-(2,6-dichloro-4-pyridyl)-2-methylhydantoic acid ethyl ester. The product was used directly for the next step. MS: 421 (MH⁺).

Step-5. NaOEt (0.16 g) was added to a solution of the compound from step-4 (1 g) in anhydrous EtOH (10 mL) at 0° C. The yellow solution was then warmed to room temperature and stirred for 1 hour. EtOH was evaporated and the residue was partitioned between EtOAc/H₂O. The combined organic layers were dried over Na₂SO₄, filtered and concentrated. The product was purified by flash chromatography on silica gel to give the titled compound. (850 mg). MS: 375 (MH⁺).

Example 2

3-(2,6-Dichloro-4-pyrydyl)-5-(4-cyanobenzyl)-1,5-dimethyl-2,4-imidazolidinedione The compound obtained in Example 1 (400 mg) and t-BuOK (180 mg) were added to a reaction flask and was then flushed with N₂. The mixture was cooled to 0° C. and THF (10 mL) was added. The reaction mixture was stirred at 0° C. for 20 minutes followed by the addition of MeI (454 mg). The reaction mixture was stirred at 0° C. for 3 hours and finally at room temperature for 1 hour. The mixture was extracted with EtOAc/H₂O. The combined organic layers were dried over Na₂SO₄, filtered and evaporated. The product was purified by prep TLC to give the titled compound (310 mg) MS: 389 (MH⁺).

Example 3

3-(2,6-Dichloro-4-pyrydyl)-5-(4-cyanobenzyl)-5-methyl-1-(5-ethoxycarbonylpentyl)-2,4-imidazolidinedione

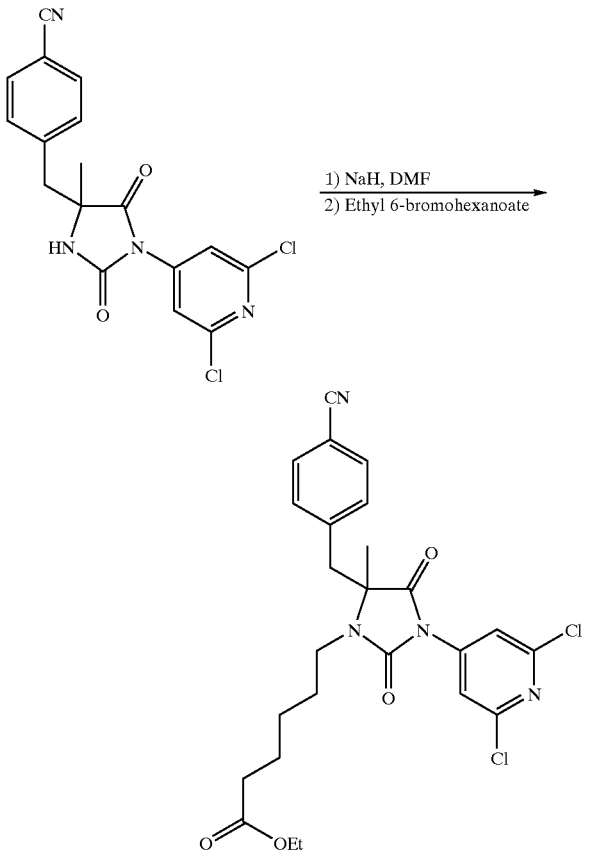

The compound obtained in Example 1 (154 mg) was taken in 2 mL anhydrous DMF. The solution was cooled to 0° C. and NaH (25 mg, 60% in oil) was added. The resulting mixture was stirred for 20 minutes at 0° C. Ethyl 6-bromohexanoate (140 mg) was added dropwise and the resulting mixture was stirred at room temperature overnight. The reaction mixture was extracted with EtOAc/H$_2$O. The combined organic layers were dried over Na$_2$SO$_4$, filtered and evaporated. The product was purified by preparative TLC to give the titled compound (180 mg). MS: 517 (MH$^+$).

Example 4

(R)-3-(2,6-Dichloro-4-pyrydyl)-5-(4-cyanobenzyl)-5-methyl-2,4-imidazolidinedione

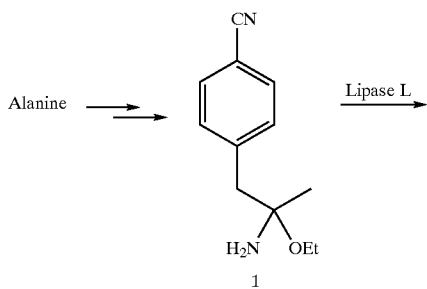

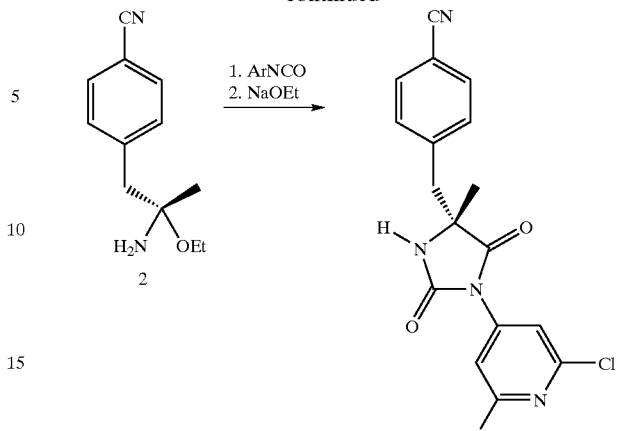

Step-1: α-Methyl-4-cyanophenylalanine ethyl ester 1 was prepared according to the methodology described in WO 98/39303.

Step-2. To a solution of the compound obtained above (770 mg) in DCM (5 mL) was added HCl (1M in Et$_2$O, 7 mL) and the reaction mixture was stirred at room temperature for 18 hours. The reaction mixture was then concentrated in vacuo to give the HCl salt of α-Methyl-4-cyanophenylalanine ethyl ester (880 mg).

Step-3. To a solution of the compound obtained above in H$_2$O (30 mL) was added a solution of KH$_2$PO$_4$ (1.4 g) in H$_2$O (30 mL). To this was added Lipase L (*Candida Lipolytica*, Sigma Aldrich, 1.4 g) and the pH of the suspension was adjusted to 6.40 using 1 N KOH. The progression of hydrolysis of ester to acid was monitored by HPLC (A=0.1% TFA in H$_2$O, B=0.1% TFA in MeCN; 15% B to 55% B over 20 minutes) with the acid eluting first (t=5.8 minutes) followed by the ester (t=10 minutes). The pH was maintained at 6.40 by the addition of further quantities of 1 N KOH until HPLC indicated the ratio of ester:acid equals 1:1.

After 31 hours, solid NaHCO$_3$ was added to bring the pH at 7.4 and the suspension was shaken with toluene (100 mL) and filtered through celite. The aqueous layer was separated and washed with DCM (2×200 mL) and the combined organics dried over MgSO$_4$. It was filtered and the filtrate was concentrated to furnish (R)-α-Methyl-4-cyanophenylalanine ethyl ester (340 mg).

Step 3: To a solution of the compound obtained above (340 mg) in DCM (10 mL) under N$_2$ at 0° C. was added neat 2,6-dichloro-4-pyridyl isocyanate (305 mg). The reaction mixture was then warmed to room temperature and stirred for 4 hours whereupon it was concentrated in vacuo to give (R)-2-(4-cyanobenzyl)-5-(2,6-dichloro-4-pyridyl)-2-methylhydantoic acid ethyl ester (680 mg).

Step-4. After flushing with N$_2$, the compound obtained above was dissolved in dry EtOH (10 mL) and NaOEt (60 mg) was added. After stirring for 3 hours, water (10 mL) and EtOAc (10 mL) were added and the mixture was shaken. The aqueous phase was then separated and washed with EtOAc (3×10 mL) and the combined organics were dried over MgSO$_4$, filtered and concentrated in vacuo. Purification by liquid chromatography (EtOAc/Hexane 1/1) gave the titled compound (410 mg). MS (m/z)=375 (M).

Example 5
3-(2,6-Dichloro-4-pyrydyl)-5-(4-cyanobenzyl)-5-methyl-1-(5-carboxypentyl)-2,4-imidazolidinedione

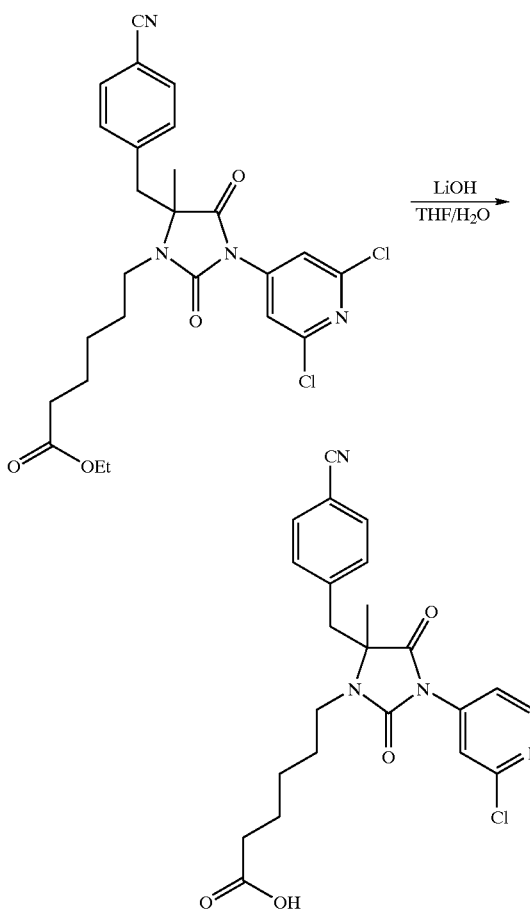

The compound obtained in Example 4 (100 mg) was dissolved in a mixture of THF/MeOH (3 mL/1 mL). A solution of LiOH (25 mg in 1 mL H$_2$O) was added and the resulting mixture was stirred at room temperature for 5 hours. The pH of the mixture was adjusted to 3–4 using 1 M HCl and the mixture was extracted with EtOAc. The combined organic layers were dried over Na$_2$SO$_4$, filtered and concentrated. The product was purified by preparative TLC to give the titled compound (80 mg). MS: 489 (MH$^+$).

Example 6
(R)-3-(2,6-Dichloro-4-pyrydyl)-5-(4-cyaznobenzyl)-1,5-dimethyl-2,4-imidazolidinedione

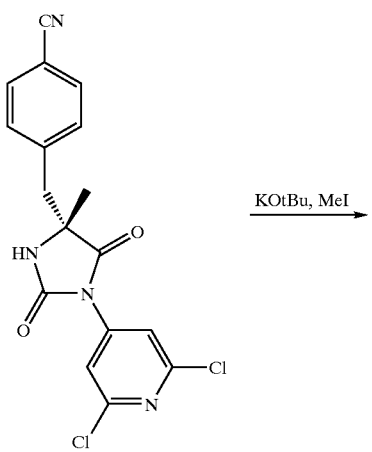

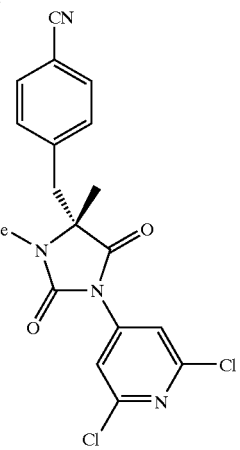

The compound obtained in Example 4 (340 mg) and KOtBu (132 mg) were weighed into a dry flask and flushed with N$_2$. The flask was placed in an ice bath and dry THF (9 mL) was added. After stirring for 15 minutes, MeI (0.17 mL) was added and the reaction mixture was warmed to room temperature. After stirring for 1 hour, water (10 mL) and EtOAc (10 mL) were added and the mixture was shaken. The aqueous phase was then separated and washed with EtOAc (3×10 mL) and the combined organics were dried over MgSO$_4$, filtered and concentrated in vacuo to give a white solid. Purification by liquid chromatography (EtOAc/Hexane=1/1) gave the titled compound (260 mg). MS (m/z)=389 (M).

The erantiomeric excess (e.e.) was determined to be >99% by chiral HPLC (0.5 mg/mL in MeOH, 3 μL, Chiracel OD#ODOOCE-11030, 250×4.6 mm, isocratic gradient, Hexane/IPA).

Example 7
(R)-3-(2,6-Dichloro-4-pyrydyl)-5-(4-bromobenzyl)-5-methyl-2,4-imidazolidinedione The titled compound was prepared in an analogous manner to that described for Example 4, using α-Methyl-4-bromophenylalanine ethyl ester which was prepared according to the methodology described in WO 98/39303. MS (m/z): 430 (MH).

Example 8
(R)-3-(2,6-Dichloro-4-pyrydyl)-5-(4-bromobenzyl)-1,5-dimethyl-2,4-imidazolidinedione The titled compound was prepared in an analogous manner to that described for Example 6. MS (m/z): 443 (MH).

The enantiomeric excess (e.e.) was determined to be >99% by chiral HPLC (0.5 mg/mL in MeOH, 3 μL, Chiracel OD#ODOOCE-11030, 250×4.6 mm, isocratic gradient, Hexane/IPA)

Example 9

3-(2,6-Dichloro-4-pyrydyl)-5-(4-hydroxybenzyl)-5-methyl-2,4-imidazolidinedione

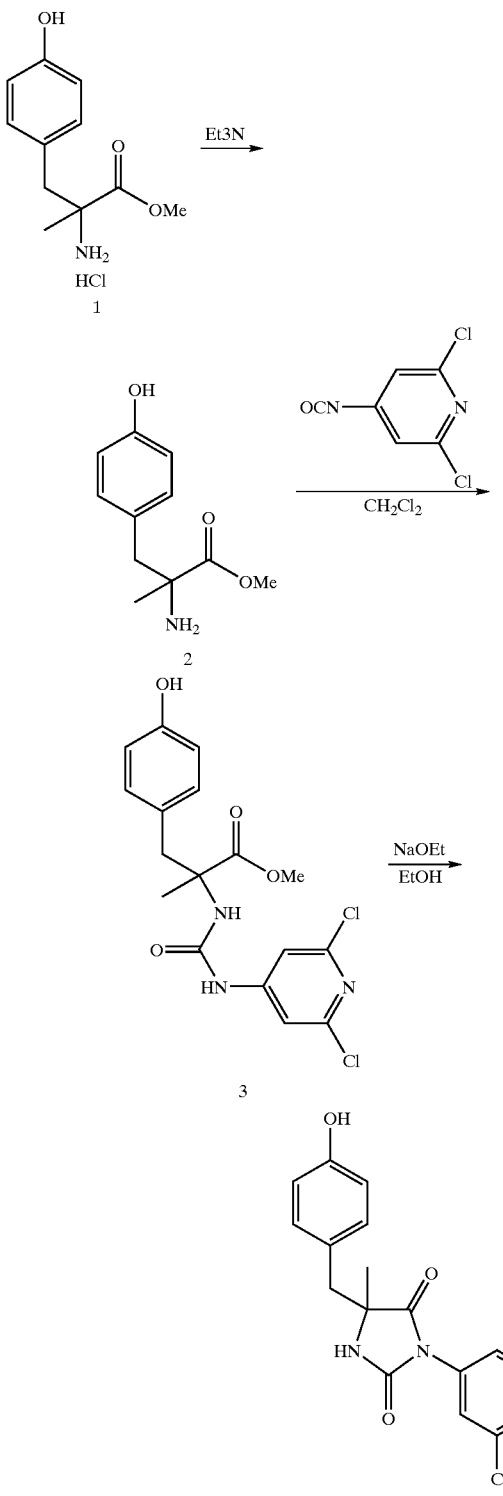

over $Na_2SO_4$, filtered and evaporated to dryness. The resulting white solid (compound 2) was used as is without purification.

Step-2. A solution of 3,5-dichloro-4-pyridyl isocyanate (0.9 g) in $CH_2Cl_2$ (5 mL) was added to a solution of the compound obtained from step-1 (1 g) in anhydrous $CH_2Cl_2$ (15 mL) containing DMF (5 mL) at 0° C. The reaction mixture was allowed to warm to room temperature and stirred overnight. The mixture was partitioned between $EtOAc/H_2O$. The combined organic layers were dried over $Na_2SO_4$, filtered and concentrated to give 2-(4-hydroxybenzyl)-5-(2,6-dichloro-4-pyridyl)-2-methylhydantoic acid methyl ester (compound 3). The product was used directly for the next step. MS: 398 ($MH^+$).

Step-3. NaOEt (0.39 g) was added to a solution of the compound from step-2 (2.26 g) in anhydrous EtOH (15 mL) at 0° C. The yellow solution was then stirred at 0° C. for 5 hours and warmed to room temperature and stirred for 1 hour. EtOH was evaporated and the residue was partitioned between $EtOAc/H_2O$. The combined organic layers were dried over $Na_2SO_4$, filtered and concentrated. The product was purified by flash chromatography on silica gel (EtOAc/hexanes 1/1) to give the titled compound (1.4 g). MS: 366 ($MH^+$).

Example 10

3-(2,6-Dichloro-4-pyrydyl)-5-(4-methoxybenzyl)-1,5-dimethyl-2,4-imidazolidinedione

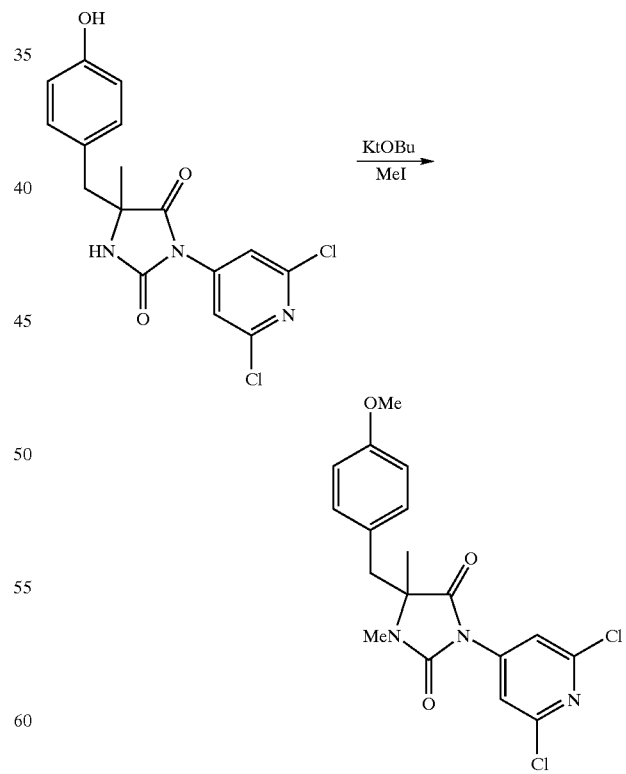

step-1. $Et_3N$ (2.47 g) was added to a solution of the compound 1 (3 g) in $H_2O$ (20 mL) and the resulting mixture was stirred for 2 hours. The solution was extracted several times with EtOAc. The combined organic layers were dried The titled compound was obtained via methylation of the compound from Example 9 by following the procedure similar to Example 2. MS: 394 ($MH^+$).

Example 11

3-(2,6-Dichloro-4-pyrydyl)-5-(4-hydroxybenzyl)-1,5-dimethyl-2,4-imidazolidinedione

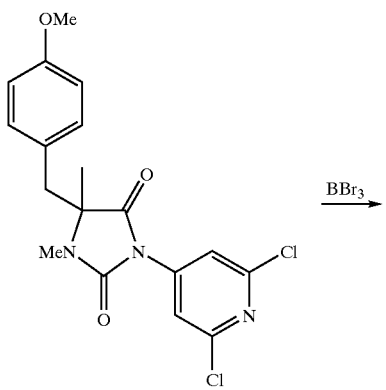

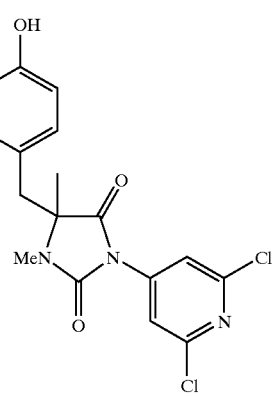

BBr$_3$ (1.14 mL, 1M in CH$_2$Cl$_2$) was added dropwise to a solution of the compound from Example 10 (0.15 g) in CH$_2$Cl$_2$ at 0° C. The resulting mixture was stirred at 0° C. for 30 minutes and then stirred for an additional 30 minutes at room temperature. The reaction was quenched with water and partitioned between EtOAc and water. The aqueous solution was extracted with EtOAc and the combined organic layers were washed with water, dried over Na$_2$SO$_4$, filtered and evaporated. The residue was purified via preparative TLC (EtOAc/Hexanes 1/1) to yield 0.125 g RBF the titled compound. MS: 380 (MH$^+$).

Example 12
3-(2,6-Dichloro-4-pyrydyl)-5-(4-i-propoxybenzyl)-1,5-dimethyl-2,4-imidazolidinedione

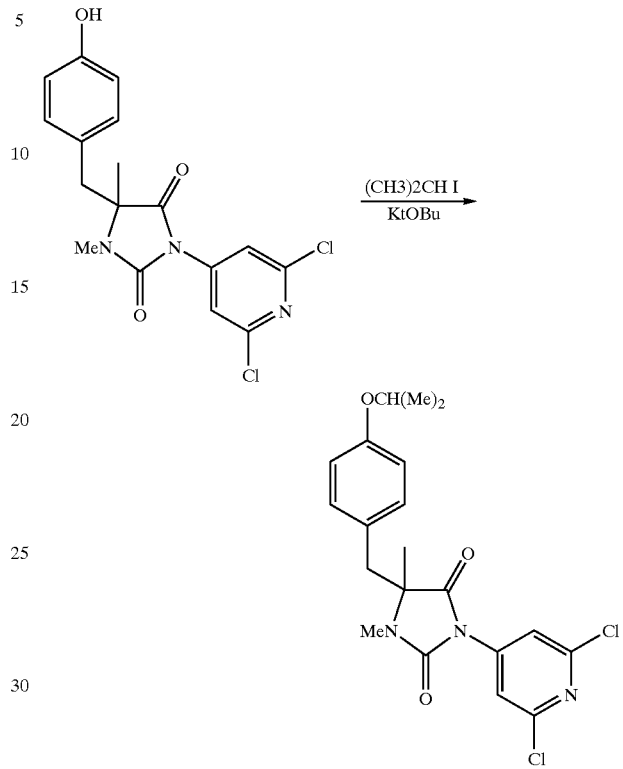

tBuOK (0.022 g) was added to a solution of the compound from Example 11 (0.06 g) in THF (3 mL) and the solution was stirred for 5 minutes. 2-Iodopropane (0.054 g) was added and the reaction mixture was refluxed for 1.5 hours. The mixture was partitioned between EtOAc/water and the EtOAc layer was dried (Na$_2$SO$_4$), filtered and evaporated. The residue was purified via preparative TLC (EtOAc/Hexanes 1/1) to give the titled compound. MS: 422 (MH$^+$).

The following compounds were prepared in a manner similar to Example 12.

TABLE 1

| Example | R$^2$ | Physiochemical Properties |
|---|---|---|
| 13 | CH$_3$(CH$_2$)$_2$O— | MS: 422 (MH$^+$) |
| 14 | CH$_3$CH$_2$O— | MS: 408 (MH$^+$) |

Example 15

3-(2,6-Dichloro-4-pyrydyl)-5-(4-ethoxy-3-fluorobenzyl)-1,5-dimethyl-2,4-imidazolidinedione

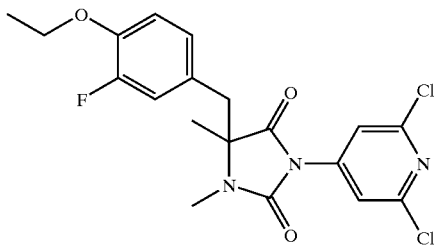

To a solution of the compound from Example 14 (0.24 g) in CH$_3$CN (15 mL) was added 3,5-dichloro-1-fluoropyridinium triflate (0.38 g) and the mixture was refluxed for 30 hours. The mixture was concentrated and purified by HPLC to give the desired compound. MS m/z 426 (MH$^+$).

Example 16

3-(2,6-Dichloro-4-pyrydyl)-5-(4-(1,1,1trifluoromethoxybenzyl)]-5-methyl-2,4-imidazolidinedione The titled compound was prepared in a manner similar to Example 1. MS: 434 (MH$^+$); mp. 151.2° C.

Example 17

3-(2,6-Dichloro-4-pyrydyl)-5-[4-(1,1,1trifluoromethoxybenzyl)]-1,5-dimethyl-2,4-imidazolidinedione The titled compound was obtained via methylation of the compound from Example 16 by following the procedure similar to Example 2. MS: 448 (MH$^+$); mp. 113.7° C.

Example 18

3-(2,6-Dichloro-4-pyrydyl)-5-(4-fluorobenzyl)]-5-methyl-2,4-imidazolidinedione

The titled compound was prepared in a manner similar to Example 1. MS: 368 (M$^+$); mp 221.1° C.

Example 19

3-(2,6-Dichloro-4-pyrydyl)-5-(4-bromobenzyl)]-5-methyl-2,4-imidazolidinedione

The titled compound was prepared in a manner similar to Example 1. MS: 429 (MH$^+$).

Example 20

3-(2,6-Dichloro-4-pyrydyl)-5-(4-bromobenzyl)]-1,5-dimethyl-2,4-imidazolidinedione The titled compound was obtained via methylation of the compound from Example 19 by following the procedure similar to Example 2. MS: 443 (MH$^+$).

Cell Adhesion Protocol

Cell Adhesion The recombinant protein ICAM-1•Fc was constructed from the 5 extracellular domains of human ICAM-1 and fusion with the constant region of human IgG. ICAM-1•Fc was purified by Protein A affinity chromatography and stored in aliquots at −20° C. Immobilized ICAM-1•Fc was prepared by dilution of the protein in PBS pH 7.5, transfer of 100 μl/well to Falcon Probind III plates and overnight incubation at 4° C. Wells coated with BSA served as a measure of non-specific background adhesion. Washed plates were blocked with a solution of 0.25% ovalbumin in PBS for 1 h at 37° C. HBSS washed Jurkat cells were suspended to a final concentration of 2.5×10$^6$/ml in TBSg adhesion buffer (24 mM Tris pH 7.4, 0.14 M NaCl, 2.7 mM KCl, 2 mM glucose, 0.1% HSA. A 100 μl volume of cells was added to the blocked and washed ICAM-1•Fc coated plates that contained 100 μl of plate buffer (TBSg, 10 mM MgCl$_{21}$, 2% DMSO). Adhesion was for 1 h at 37° C. Non-adherent cells were removed using the EL404 plate washer (BioTek Instruments; Highland Park, Vt.). The number of adherent cells was quantified by measuring enzymatic activity of endogenous N-acetyl-hexosaminidase using the enzyme substrate p-nitrophenol-N-acetyl-b-D-glucoseaminide, pNAG. The amount of liberated p-nitrophenol was measured by reading the optical density at 405 nm using a vertical pathway spectrophotometer to quantify cell attachment (VMAX Kinetic Microplate Reader, Molecular Devices, Menlo Park, Calif.). For competition studies the compounds from 100% DMSO stock solutions were diluted in plate buffer at 2-fold the required testing concentration prior to transfer to the ICAM-1-Fc coated plate and serial dilution.

What is claimed is:

1. A compound of the formula (I):

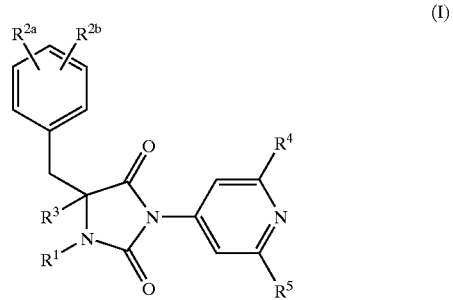

(I)

or a pharmaceutically acceptable salt thereof, wherein R$^1$ is selected from
  1) hydrogen atom, or
  2) a C$_{1-6}$ alkyl group which may be optionally substituted with carboxyl group or a C$_{1-6}$ alkoxycarbonyl group;
    R$^{2a}$ and R$^{2b}$ are independently hydrogen atom, hydroxyl group, cyano group, a C$_{1-6}$ alkythio group which may be optionally substituted with 1 to 3 halogen atoms, a C$_{1-6}$ alkylsulfinyl group which may be optionally substituted with 1 to 3 halogen atoms, a C$_{1-6}$ alkylsulfonyl group which may be optionally substituted with 1 to 3 halogen atoms, or a C$_{1-6}$ alkoxy group which may be optionally substituted with 1 to 3 halogen atoms;
    R$^3$ is a C$_{1-6}$ alkyl group; and
    R$^4$ and R$^5$ are independently a halogen atom.

2. The compound according to claim 1, wherein R$^1$ is hydrogen atom or a C$_{1-6}$ alkyl group which may be optionally substituted with carboxyl group or a C$_{1-6}$ alkoxycarbonyl group, R$^{2a}$ and R$^{2b}$ are independently hydrogen atom, hydroxyl group, cyano group or a C$_{1-6}$ alkoxy group which may be optionally substituted with 1–3 halogen atoms, R$^3$ is a C$_{1-6}$ alkyl group, and R$^4$ and R$^5$ are independently a halogen atom.

3. The compound according to claim 2, wherein R$^1$ is hydrogen atom or a C$_{1-6}$ alkyl group, one of R$^{2a}$ and R$^{2b}$ is hydrogen atom, and the other is a cyano group, or a $C_{1-6}$ alkoxy group which may be optionally substituted with 1–3 halogen atoms, $R^3$ is a $C_{1-6}$ alkyl group, and $R^4$ and $R^5$ are independently a halogen atom.

4. The compound according to claim 3, wherein $R^1$ is hydrogen atom or methyl group, one of $R^{2a}$ and $R^{2b}$ is hydrogen atom and the other is cyano group, a $C_{1-6}$ alkoxy group or trifluoromethoxy group, $R^3$ is methyl group, $R^4$ and $R^5$ are chlorine atom.

5. The compound according to claim 2, wherein $R^1$ is a $C_{1-6}$ alkyl group which is substituted with a $C_{1-6}$ alkoxycarbonyl group or carboxyl group, one of $R^{2a}$ and $R^{2b}$ is hydrogen atom, and the other is a cyano group, or $C_{1-6}$ alkoxy group which may be optionally substituted with 1–3 halogen atoms, $R^3$ is a $C_{1-6}$ alkyl group, and $R^4$ and $R^5$ are independently a halogen atom.

6. The compound according to claim 5, $R^3$ is methyl group, and $R^4$ and $R^5$ are chlorine atom.

7. The compound according to claim 1, wherein the compound is selected from:

3-(2,6-Dichloro-4-pyrydyl)-5-(4-propoxybenzyl)-1,5-dimethyl-2,4-imidazolidinedione, 3-(2,6-Dichloro-4-pyrydyl)-5-(4-ethoxybenzyl)-1,5-dimethyl-2,4-imidazolidinedione, 3-(2,6-dichloro-4-pyrydyl)-5-(4-(1,1,1trifluoromethoxybenzyl)]-5-methyl-2,4-imidazolidinedione, 3-(2,6-dichloro-4-pyrydyl)-5-[4-(1,1,1trifluoromethoxybenzyl)]-1,5-Dimethyl-2,4-imidazolidinedione, 3-(2,6-Dichloro-4-pyrydyl)-5-(4-Cyanobenzyl)-5-methyl-2,4-imidazolidinedione, 3-(2,6-Dichloro-4-pyrydyl)-5-(4-Cyanobenzyl)-1,5-dimethyl-2,4-imidazolidinedione; and a pharmaceutically acceptable salt of these compounds.

8. A process for preparing a compound of the formula (I-a):

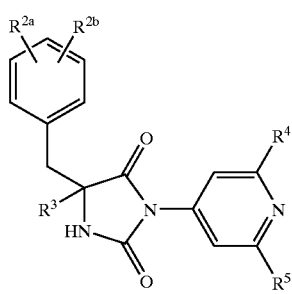

(I-a)

or a pharmaceutically acceptable salt thereof, wherein $R^{2a}$ and $R^{2b}$ are independently hydrogen atom, hydroxyl group, cyano group, a $C_{1-6}$ alkylthio group which may be optionally substituted with 1 to 3 halogen atoms, a $C_{1-6}$ alkylsulfinyl group which may be optionally substituted with 1 to 3 halogen atoms, a $C_{1-6}$ alkylsulfonyl group which may be optionally substituted with 1 to 3 halogen atoms, or a $C_{1-6}$ alkoxy group which may be optionally substituted with 1 to 3 halogen atoms;

$R^3$ is a $C_{1-6}$ alkyl group;

$R^4$ and $R^5$ are independently a halogen atom;

which comprises cyclizing the compound of the formula (II):

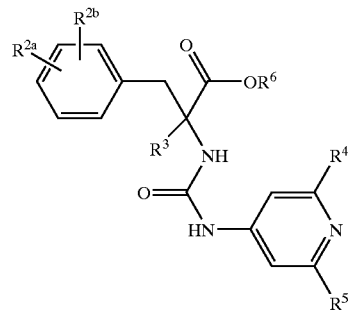

(II)

wherein $OR^6$ is a hydroxyl group or a protected hydroxyl group, and the other symbols are the same as defined above, and converting into the pharmaceutically acceptable salt, if necessary.

9. A process for preparing a compound of the formula (I-b):

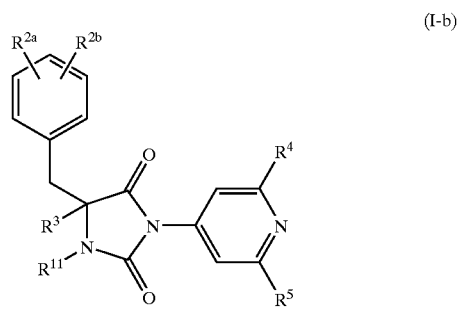

(I-b)

or a pharmaceutically acceptable salt thereof, wherein $R^{11}$ is a $C_{1-6}$ alkyl group which may be optionally substituted with carboxyl group or a $C_{1-6}$ alkoxycarbonyl group;

$R^{2a}$ and $R^{2b}$ are independently hydrogen atom, hydroxyl group, cyano group, a $C_{1-6}$ alkylthio group which may be optionally substituted with 1 to 3 halogen atoms, a $C_{1-6}$ alkylsulfinyl group which may be optionally substituted with 1 to 3 halogen atoms, a $C_{1-6}$ alkylsulfonyl group which may be optionally substituted with 1 to 3 halogen atoms, or a $C_{1-6}$ alkoxy group which may be optionally substituted with 1 to 3 halogen atoms;

$R^3$ is a $C_{1-6}$ alkyl group;

$R^4$ and $R^5$ are independently a halogen atom;

which comprises (1) alkylating a compound of the formula (I-a):

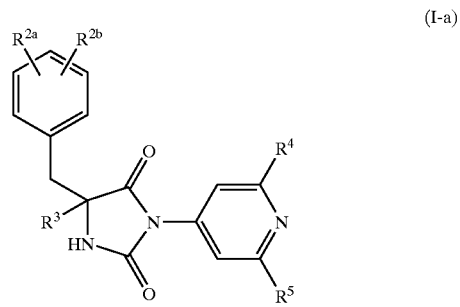

(I-a)

wherein the symbols are the same as defined above, (2) hydrolyzing the resulting compound, if necessary, and
(3) converting into the pharmaceutically acceptable salt, if further desired.

10. A process for preparing a compound of the formula (I-c):

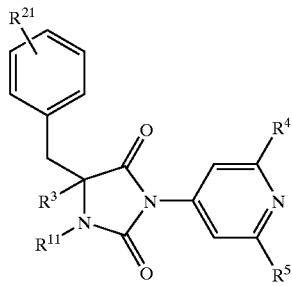

or a pharmaceutically acceptable salt thereof, wherein
$R^{11}$ is a $C_{1-6}$ alkyl group which may be optionally substituted with carboxyl group or a $C_{1-6}$ alkoxycarbonyl group;
$R^{21}$ is a $C_{1-6}$ alkoxy group which may be optionally substituted with 1 to 3 halogen atoms;
$R^3$ is a $C_{1-6}$ alkyl group;
$R^4$ and $R^5$ are independently a halogen atom;
which comprises alkylating a compound of the formula (I-d):

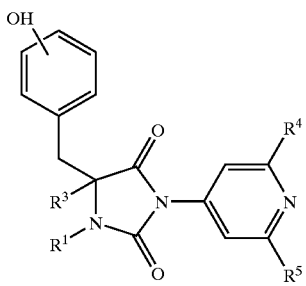

wherein $R^1$ is hydrogen atom or a $C_{1-6}$ alkyl group which may be optionally substituted with carboxyl group or a $C_{1-6}$ alkoxycarbonyl group, and the other symbols are the same as defined above, and converting into the pharmaceutically acceptable salt, if necessary.

11. A pharmaceutical composition which comprises a therapeutically effective amount of the compound as set forth in any one of claims 1–7 in admixture with a therapeutically acceptable carrier or diluent.

12. A method for treatment or prevention of $\alpha_L\beta_2$ adhesion mediated condition in a mammal comprising administering a therapeutically effective amount of the compound as set forth in any one of claims 1–7.

13. The method according to claim 12, said condition is selected from rheumatoid arthritis, asthma, allergy conditions, adult respiratory distress syndrome, AIDS, cardiovascular diseases, thrombosis, harmful platelet aggregation, reocclusion following thrombolysis, reperfusion injury, skin inflammatory diseases, osteoporosis, osteoarthritis, arteriosclerosis, neoplastic diseases, wound, detaching retina, Type I diabetes, multiple sclerosis, systemic lupus erythematosus, ophthalmic inflammatory conditions, inflammatory bowel diseases, regional enteritis, Sjogren's Syndrome, and rejection after transplantation.

14. The method according to claim 13, wherein said diseases is selected from psoriasis, rheumatoid arthritis, inflammatory bowel diseases (Crohn's disease, ulcerative colitis), systemic lupus erythematosus, atopic dermatitis, Sjogren's Syndrome, rejection after transplantation (allograft rejection and graft vs. host disease).

* * * * *